United States Patent
Kameya et al.

(10) Patent No.: US 9,855,196 B2
(45) Date of Patent: Jan. 2, 2018

(54) DENTAL CURABLE COMPOSITION AND DENTAL FLOWABLE COMPOSITE RESIN

(71) Applicant: KURARAY NORITAKE DENTAL INC., Kurashiki-shi (JP)

(72) Inventors: Takehiro Kameya, Tainai (JP); Hiroshige Ishino, Tainai (JP); Akiko Tsuji, Kurashiki (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 0 days.

(21) Appl. No.: 14/648,536

(22) PCT Filed: Nov. 26, 2013

(86) PCT No.: PCT/JP2013/006945
§ 371 (c)(1),
(2) Date: May 29, 2015

(87) PCT Pub. No.: WO2014/083842
PCT Pub. Date: Jun. 5, 2014

(65) Prior Publication Data
US 2015/0320646 A1    Nov. 12, 2015

(30) Foreign Application Priority Data

Nov. 30, 2012  (JP) ................................. 2012-262884

(51) Int. Cl.
| | | |
|---|---|---|
| A61K 6/08 | (2006.01) | |
| A61K 6/083 | (2006.01) | |
| A61C 19/02 | (2006.01) | |
| A61K 6/027 | (2006.01) | |
| A61K 6/00 | (2006.01) | |
| A61C 5/50 | (2017.01) | |

(52) U.S. Cl.
CPC ............... *A61K 6/083* (2013.01); *A61C 5/50* (2017.02); *A61C 19/02* (2013.01); *A61K 6/0005* (2013.01); *A61K 6/0008* (2013.01); *A61K 6/0017* (2013.01); *A61K 6/0073* (2013.01); *A61K 6/027* (2013.01); *A61K 6/0276* (2013.01)

(58) Field of Classification Search
CPC .................................................. A61K 6/0008
See application file for complete search history.

(56) References Cited

U.S. PATENT DOCUMENTS

| | | | |
|---|---|---|---|
| 6,849,670 B2 | 2/2005 | Satoh et al. | |
| 7,951,851 B2 | 5/2011 | Kuboe et al. | |
| 8,476,338 B2 | 7/2013 | Okubayashi et al. | |
| 2003/0162863 A1* | 8/2003 | Satoh | A61K 6/0052 523/109 |
| 2008/0015522 A1* | 1/2008 | Yeshurun | A61M 5/19 604/272 |
| 2011/0257292 A1* | 10/2011 | Okubayashi | A61K 6/0005 523/115 |

FOREIGN PATENT DOCUMENTS

| | | |
|---|---|---|
| CN | 101600412 A | 12/2009 |
| CN | 102341088 A | 2/2012 |
| JP | 2002-518309 A | 6/2002 |
| JP | 2011-190254 A | 9/2011 |
| WO | 99/65453 A1 | 12/1999 |
| WO | 02/05752 A1 | 1/2002 |
| WO | 2008/093596 A1 | 8/2008 |
| WO | 2011/074222 A1 | 6/2011 |

OTHER PUBLICATIONS

Combined Chinese Office Action and Search Report dated Nov. 14, 2016 in Patent Application No. 201380062443.7.
Zhang Zhenkang, et al., "Modern stomatology", vol. I, II, Science Press, 2003; pp. 2343-2345 and Cover Pages (with English translation).
International Search Report dated Feb. 25, 2014 in PCT/JP13/006945 Filed Nov. 26, 2013.

* cited by examiner

*Primary Examiner* — Michael Pepitone
(74) *Attorney, Agent, or Firm* — Oblon, McClelland, Maier & Neustadt, L.L.P.

(57) ABSTRACT

The present invention provides a dental curable composition suitable as a flowable composite resin. The dental curable composition, when in the form of a cured product, has excellent mechanical strength, polishability, and gloss retention, and, when in the form of a paste, has consistency appropriate for discharge through a needle attached to the tip of a syringe and exhibits good formability and handling properties after discharge through the needle. The present invention is a dental curable composition including: a polymerizable monomer (A); irregularly-shaped inorganic particles (B) having an average particle diameter of 0.1 to 0.3 μm and surface-treated with a silane coupling agent having a particular structure; and inorganic ultrafine particles (C) having an average particle diameter of 5 to 50 nm and surface-treated with a silane coupling agent having a particular structure, the dental curable composition containing 92.5 to 98 weight % of the irregularly-shaped inorganic particles (B) and 2 to 7.5 weight % of the inorganic ultrafine particles (C) relative to the amount of total inorganic particles and having a consistency of 25 to 55.

16 Claims, No Drawings

DENTAL CURABLE COMPOSITION AND DENTAL FLOWABLE COMPOSITE RESIN

CROSS REFERENCE TO RELATED APPLICATIONS

This application is a 35 U.S.C. §371 national stage patent application of international patent application PCT/JP13/006945, filed on Nov. 26, 2013, the entire text of which is incorporated by reference, and claims priority to Japanese patent application JP 2012-262884, filed on Nov. 30, 2012, the entire text of which is also incorporated by reference.

TECHNICAL FIELD

The present invention relates to a dental material capable of serving as a substitute for a part or the whole of a natural tooth in the field of dentistry, particularly a dental curable composition that can be suitably used as a dental flowable composite resin.

BACKGROUND ART

Dental curable compositions composed of a polymerizable monomer, a filler, and a polymerization initiator are called composite resins, and are dental materials most widely used today as materials for restoring lost portions of teeth or carious teeth. The composite resins, when in the form of a cured product having undergone polymerization and curing, are required to have characteristics such as mechanical strength sufficient for substitution for natural teeth, polishability for obtaining gloss comparable to that of natural teeth, and gloss retention. When in the form of a paste that has yet to be polymerized and cured, they are required to have characteristics such as formability and handling properties appropriate for the operation of filling cavities by use of a dental instrument.

In recent years, composite resins called flowable composite resins, which have high flowability before being polymerized and cured, have also been developed. The flowable composite resins are used in the form of a paste for a treatment in which a cavity is filled with the paste by injecting the paste directly through a needle having an orifice with a diameter smaller than that of the cavity and attached to the tip of a container (syringe) holding the paste. The flowable composite resins make it possible to perform the filling operation simply by feeding a paste into a cavity from a syringe, and thereby allow reduction in the treatment time. Therefore, the use of flowable composite resins is becoming increasingly widespread in clinical practice.

In order for a dental curable composition to function as a flowable composite resin, the dental curable composition is required not only to have sufficient levels of mechanical strength, polishability, and gloss retention which are required of common composite resins when it is in the form of a cured product, but also to exhibit a level of flowability characteristic of flowable composite resins when it is in the form of a paste; that is, a paste of the dental curable composition is required to have a level of consistency appropriate for discharge through a needle attached to the tip of a syringe and to exhibit a level of formability and handling properties after discharge through the needle. What has the largest influence on these required characteristics is the filler contained in the dental curable composition. However, these required characteristics are mutually related to each other. That is, changing the filler to improve one of the characteristics leads to deterioration in another of the characteristics. Therefore, it is difficult to achieve high levels of the required characteristics all together. To this end, various attempts have been made thus far.

For example, Patent Literature 1 discloses a dental curable composition mainly intended to be used as a flowable composite resin. The dental curable composition is a blend of a polymerizable monomer with two types of fillers, one of which consists of irregularly-shaped inorganic particles having an average particle diameter of 1.0 to 5.0 μm and surface-treated with a silane coupling agent having a particular structure, and the other of which consists of inorganic fine particles having an average particle diameter of 0.01 to 0.10 μm and surface-treated with a silane coupling agent having a particular structure. The dental curable composition has good formability and consistency when in the form of a paste, and has excellent mechanical strength when in the form of a cured product. As a result of study by the present inventors, however, the dental curable composition of Patent Literature 1 has been found to have room for improvement in terms of the polishability and gloss retention.

Dental materials or dental compositions usable as a composite resin and containing a combination of two types of surface-treated fillers having different particle diameters are disclosed in Patent Literature 2 to 4. However, Patent Literature 2 to 4 do not include any disclosure concerning flowable composite resins, and the materials or compositions discussed in the examples of Patent Literature 2 to 4 are those which, when in the form of a paste, do not have an appropriate level of flowability as a flowable composite resin or those which have room for improvement in terms of the polishability, gloss retention, etc.

CITATION LIST

Patent Literature

Patent Literature 1: WO 2008/093596 A1
Patent Literature 2: JP 2002-518309 A
Patent Literature 3: WO 2002/05752 A1
Patent Literature 4: WO 2011/074222 A1

SUMMARY OF INVENTION

Technical Problem

Under such circumstances, the present invention aims to provide a dental curable composition suitable as a flowable composite resin. The dental curable composition, when in the form of a cured product, has excellent mechanical strength, polishability, and gloss retention, and, when in the form of a paste, has consistency appropriate for discharge through a needle attached to the tip of a syringe and exhibits good formability and handling properties after discharge through the needle.

Solution to Problem

The present invention is a dental curable composition including:
a polymerizable monomer (A);
irregularly-shaped inorganic particles (B) having an average particle diameter of 0.1 to 0.3 μm and surface-treated with a silane coupling agent (a) represented by the formula (1) below (in which $R^1$ represents a hydrogen atom or a methyl group, $R^2$ represents a hydrolyzable group, $R^3$ represents a hydrocarbon group having 1 to 6 carbon atoms, p is an integer of 2 or 3, and q is an integer of 8 to 13); and inorganic ultrafine particles (C) having an average particle diameter of 5 to 50 nm and surface-treated with a silane coupling agent (b) represented by a formula that is the same as the formula (1) representing the silane coupling agent (a) except that q is an integer of 1 to 6, the dental curable composition containing 92.5 to 98 weight % of the irregularly-shaped inorganic particles (B) and 2 to 7.5 weight % of the inorganic ultrafine particles (C) relative to the amount of total inorganic particles, the dental curable composition having a consistency of 25 to 55.

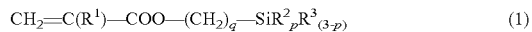

$$CH_2=C(R^1)-COO-(CH_2)_q-SiR^2_p R^3_{(3-p)} \quad (1)$$

In a preferred embodiment of the dental curable composition of the present invention, the polymerizable monomer (A) has a refractive index after polymerization of 1.52 to 1.58, the irregularly-shaped inorganic particles (B) have a refractive index of 1.52 to 1.58, and the inorganic ultrafine particles (C) have a refractive index of 1.43 to 1.50.

The dental curable composition of the present invention preferably contains 25 to 50 parts by weight of the polymerizable monomer (A) per 100 parts by weight of the amount of total inorganic particles.

In a preferred embodiment of the dental curable composition of the present invention, the inorganic ultrafine particles (C) are present in the form of agglomerated particles, and the agglomerated particles have an average particle diameter of 1 to 10 μm.

The present invention is also a dental flowable composite resin including the above dental curable composition.

The present invention is also a package including a container holding the above dental flowable composite resin and a needle chip to be attached to a tip of the container.

Advantageous Effects of Invention

The dental curable composition of the present invention, when in the form of a cured product, has excellent mechanical strength, polishability, and gloss retention, and, when in the form of a paste, has consistency appropriate for discharge through a needle attached to the tip of a syringe and exhibits good formability and handling properties after discharge through the needle. Therefore, the dental curable composition is suitable as a flowable composite resin.

DESCRIPTION OF EMBODIMENTS

A conventional composite resin used as a dental curable composition cannot, due to the high viscosity of the composition, be directly injected from a container holding the composition to fill a cavity of a tooth. Usually, when tooth filling operation is performed using the composition, an appropriate amount of the composition is taken out of the container, then loaded into a cavity by means of a dental filling device such as a dental instrument, formed into a shape conforming to the cavity, and cured. By contrast, a recently-developed composite resin used for tooth filling operation is a composition that is injected to fill a cavity directly through a needle having an orifice with a diameter smaller than that of the cavity and attached to the tip of a container (syringe) holding the composition and that is then shaped and cured. The latter is referred to as a "flowable composite resin" in the present description.

Two types of flowable composite resins differing in consistency have been generally used. In the present description, as is customary in the field of dental materials, a type of flowable composite resin whose consistency has been set relatively low to enhance its formability is referred to as a "low-flow" type, while a type of flowable composite resin whose consistency has been set relatively high to slightly reduce its formability and ensure its flowability is referred to as a "high-flow" type.

First, a polymerizable monomer (A), irregularly-shaped inorganic particles (B), and inorganic ultrafine particles (C), which are essential components of the dental curable composition of the present invention, will be described.

Polymerizable Monomer (A)

As the polymerizable monomer (A) used in the present invention, a commonly-known polymerizable monomer can be used without any limitation. One monomer or a mixture of two or more monomers can be used as the polymerizable monomer (A). The polymerizable monomer (A) has a refractive index after polymerization of preferably 1.52 to 1.58, more preferably 1.525 to 1.58, even more preferably 1.53 to 1.58, because in these cases the refractive index can easily be made close to the refractive index of the irregularly-shaped inorganic particles (B). In the present description, the "refractive index" refers to a refractive index measured with an Abbe refractometer at 25° C. In addition, "refractive index after polymerization" of the polymerizable monomer (A) refers to the refractive index of a polymer of the polymerizable monomer (A). In order to obtain a desired value of the refractive index after polymerization of the polymerizable monomer (A), it is only necessary to select a single type of polymerizable monomer or to mix several types of polymerizable monomers having different refractive indices in proper proportions while taking into account the fact that a polymer of a polymerizable monomer generally tends to have a slightly higher refractive index than the polymerizable monomer.

As the polymerizable monomer (A), a radical-polymerizable monomer is suitably used. Specific examples of the radical-polymerizable monomer used as the polymerizable monomer (A) include: esters of α-cyanoacrylic acid, (meth)acrylic acid, α-halogenated acrylic acid, crotonic acid, cinnamic acid, sorbic acid, maleic acid, and itaconic acid; (meth)acrylamide; (meth)acrylamide derivatives; vinyl esters; vinyl ethers; mono-N-vinyl derivatives; and styrene derivatives. Among these, (meth)acrylic acid esters and (meth)acrylamide derivatives are preferable, and (meth)acrylic acid esters are more preferable. In the present invention, the wording "(meth)acryl" is intended to embrace both "methacryl" and "acryl".

Examples of the polymerizable monomer which is a (meth)acrylic acid ester or a (meth)acrylamide derivative are given below.

(I) Monofunctional (Meth)Acrylates and Monofunctional (Meth)Acrylamide Derivatives Examples include methyl (meth)acrylate, isobutyl (meth)acrylate, benzyl (meth)acrylate, lauryl (meth)acrylate, 2,3-dibromopropyl (meth)acrylate, 2-hydroxyethyl (meth)acrylate, 6-hydroxyhexyl (meth)acrylate, 10-hydroxydecyl (meth)acrylate, propylene glycol mono(meth)acrylate, glycerin mono(meth)acrylate, erythritol mono(meth)acrylate, N-methylol(meth)acrylamide, N-hydroxyethyl(meth)acrylamide, N-(dihydroxyethyl)(meth)acrylamide, (meth)acryloyloxydodecylpyridinium bromide, (meth)acryloyloxydecylpyridinium chloride, (meth)acryloyloxyhexadecylpyridinium chloride, and (meth)acryloyloxydecylammonium chloride.

(II) Difunctional (Meth)Acrylates

Examples include ethylene glycol di(meth)acrylate, triethylene glycol di(meth)acrylate, propylene glycol di(meth)acrylate, neopentyl glycol di(meth)acrylate, 1,6-hexanediol di(meth)acrylate, 1,10-decanediol di(meth)acrylate, 2,2-bis

[4-[3-(meth)acryloyloxy-2-hydroxypropoxy]phenyl]propane (generally called "Bis-GMA"), 2,2-bis[4-(meth)acryloyloxyethoxypheny]propane, 2,2-bis[4-(meth)acryloyloxypolyethoxyphenyl]propane, 1,2-bis[3-(meth)acryloyloxy-2-hydroxypropoxy]ethane, pentaerythritol di(meth)acrylate, and [2,2,4-trimethylhexamethylene bis(2-carbamoyloxyethyl)]dimethacrylate (generally called "UDMA").

(III) Tri- or Higher-Functional (Meth)Acrylates

Examples include trimethylolpropane(meth)acrylate, trimethylolethane tri(meth)acrylate, tetramethylolmethane tri(meth)acrylate, pentaerythritol tetra(meth)acrylate, dipentaerythritol hexa(meth)acrylate, N,N'-(2,2,4-trimethylhexaraethylene)bis[2-(aminocarboxy)propane-1,3-diol]tetramethacrylate, and 1,7-diacryloyloxy-2,2,6,6-tetraacryloyloxymethyl-4-oxyheptane.

Among the above-mentioned polymerizable monomers, the following are preferably used as the polymerizable monomer (A) in the present invention in terms of the refractive index after polymerization and the handling properties of the resulting paste: triethylene glycol di(meth)acrylate, neopentyl glycol di(meth)acrylate, 1,6-hexanediol di(meth)acrylate, 1,10-decanediol di(meth)acrylate, 2,2-bis[4-[3-(meth)acryloyloxy-2-hydroxypropoxy]phenyl]propane, 2,2-bis[4-(meth)acryloyloxyethoxypheny]propane, [2,2,4-trimethylhexamethylene bis(2-carbamoyloxyethyl)]dimethacrylate, and N,N'-(2,2,4-trimethylhexamethylene)bis[2-(aminocarboxy)propane-1,3-diol]tetramethacrylate.

Furthermore, in terms of ease of adjustment of the refractive index after polymerization and the handling properties of the resulting paste, it is preferable that, when the amount of the total polymerizable monomer (A) is assumed to be 100 parts by weight, the polymerizable monomer (A) contain: 40 to 85 parts by weight of 2,2-bis[4-(meth)acryloyloxypolyethoxypheny]propane; 10 to 50 parts by weight of at least one selected from the group consisting of triethylene glycol di(meth)acrylate, neopentyl glycol di(meth)acrylate, 1,6-hexanediol di(meth)acrylate, and 1,10-decanediol di(meth)acrylate; and 0 to 25 parts by weight of at least one selected from the group consisting of 2,2-bis[4-[3-(meth)acryloyloxy-2-hydroxypropoxy]phenyl]propane, [2,2,4-trimethylhexamethylene bis(2-carbamoyloxyethyl)]dimethacrylate, and N,N'-(2,2,4-trimethylhexamethylene)bis[2-(aminocarboxy)propane-1,3-diol]tetramethacrylate.

The content of the polymerizable monomer (A) is preferably 25 to 50 parts by weight, more preferably 28 to 47 parts by weight, and even more preferably 30 to 45 parts by weight, per 100 parts by weight of the amount of total inorganic particles. The content less than 25 parts by weight may lead to a situation where the resulting paste has a consistency too low for use as a flowable composite resin, and cannot be extruded when discharged from a syringe through a needle due to too high a discharge force. The content more than 50 parts by weight may lead to a situation where the amount of inorganic particles is insufficient, with the result that a dental curable composition exhibiting sufficient mechanical strength cannot be obtained. The "amount of total inorganic particles" refers to the sum of the amounts of the irregularly-shaped inorganic particles (B), the inorganic ultrafine particles (C), and optionally-added inorganic material particles other than the irregularly-shaped inorganic particles (B) and the inorganic ultrafine particles (C).

In the present invention, the viscosity of the polymerizable monomer (A) is preferably 20 to 400 mPa·s, and more preferably 40 to 200 mPa·s at 40° C., in order for the resulting flowable composite resin to have handling properties suitable for direct injection. When two or more types of polymerizable monomers are used, the viscosity of the total polymerizable monomers can be expressed as a weighted average of the viscosities of the polymerizable monomers. The average of the viscosities is preferably 20 to 400 mPa·s, and more preferably 40 to 200 mPa·s at 40° C. The viscosity of the polymerizable monomer (A) can be measured, for example, with a cone-plate viscometer (e.g., TV-30 viscometer manufactured by Toki Sangyo Co., Ltd.).

Irregularly-Shaped Inorganic Particles (B)

The irregularly-shaped inorganic particles (B) used in the present invention are irregularly-shaped particles surface-treated with a silane coupling agent (a) having a long alkyl chain and represented by the formula (1) below, and have an average particle diameter of 0.1 to 0.3 μm.

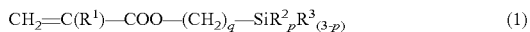

$$CH_2=C(R^1)-COO-(CH_2)_q-SiR^2_p R^3_{(3-p)} \qquad (1)$$

In the formula, $R^1$ represents a hydrogen atom or a methyl group, $R^2$ represents a hydrolyzable group, $R^3$ represents a hydrocarbon group having 1 to 6 carbon atoms, p is an integer of 2 or 3, and q is an integer of 8 to 13.

If spherical inorganic particles are used, the mechanical strength of the cured product will be reduced, since they have a reduced specific surface area and thereby decreased binding properties to the polymerizable monomer, as compared with irregularly-shaped particles. Therefore, in the present invention, the inorganic particles (B) have irregular shapes.

If the average particle diameter of the irregularly-shaped particles is less than 0.1 μm, although the polishability of a cured product of the composition may be sufficient, the consistency of a paste of the composition is likely to be low, and a paste with a consistency of 25 to 50 suitable for use as a flowable composite resin cannot be obtained. Furthermore, increasing the filler content is difficult, which leads to a reduction in mechanical strength. If the average particle diameter is more than 0.3 μm, although sufficient mechanical strength may be obtained, the polishability will be reduced. Particularly, the long-term polishability, that is, the gloss retention, which is important for clinical practice, will be reduced early if the average particle diameter is more than 0.3 μm. In clinical practice, polishing the cured product for a long period of time (1 minute or longer per tooth) to obtain good gloss is not preferred because such polishing increases the treatment time; however, if the average particle diameter is more than 0.3 μm, the polishability for restoring the initial gloss will be reduced, and therefore a long treatment time will be required. In terms of the mechanical strength, polishability, and gloss retention of the cured product and the handling properties of the paste, the average particle diameter of the irregularly-shaped inorganic particles (B) is preferably 0.12 to 0.25 μm, and more preferably 0.15 to 0.2 μm. The average particle diameter of the irregularly-shaped inorganic particles (B) can be determined by laser diffraction scattering. Specifically, for example, the average particle diameter can be measured using a laser diffraction particle size analyzer (SALD-2100 manufactured by Shimadzu Corporation) and using a 0.2% aqueous sodium hexametaphosphate solution as a dispersion medium.

It is known that, in general, treating the surfaces of inorganic particles with a silane coupling agent causes hydrophobization of the surfaces of the inorganic particles and thereby provides an improvement in the affinity for a polymerizable monomer, thus making it possible to increase the content of the inorganic particles in the composition. Even if the irregularly-shaped inorganic particles (B) having an average particle diameter of 0.1 to 0.3 μm are surface-treated with a silane coupling agent having a short alkyl chain (e.g., the silane coupling agent (b) described later), the content of the irregularly-shaped inorganic particles (B) can be increased indeed. However, if the irregularly-shaped inorganic particles (B) thus surface-treated are contained in an amount large enough to provide sufficient strength, the resulting paste can only have a consistency of 20 or less, which means that a consistency appropriate for a flowable composite resin that can be directly injected to fill a tooth (a consistency of 25 to 55) is not achieved. When the irregularly-shaped inorganic particles (B) having an average particle diameter of 0.1 to 0.3 μm are surface-treated with the silane coupling agent (a) having a long alkyl chain, the hydrophobicity of the surfaces of the irregularly-shaped inorganic particles (B) becomes very high, and the affinity for the polymerizable monomer (A) is increased. Accordingly, it is possible to increase the content of the irregularly-shaped inorganic particles (B) and thus obtain a flowable composite resin exhibiting high mechanical strength while ensuring the consistency of 25 to 55. In addition, the increase in surface hardness provides an improvement in polishability.

In the silane coupling agent (a) represented by the above general formula (1), $R^1$ represents a hydrogen atom or a methyl group, $R^2$ represents a hydrolyzable group, $R^3$ represents a hydrocarbon group having 1 to 6 carbon atoms, p is an integer of 2 or 3, and q is an integer of 8 to 13. Examples of the hydrolyzable group represented by $R^2$ include: alkoxy groups such as methoxy, ethoxy, and butoxy groups; a chlorine atom; and an isocyanate group. Examples of the hydrocarbon group having 1 to 6 carbon atoms and represented by $R^3$ include alkyl groups having 1 to 6 carbon atoms, alkenyl groups having 2 to 6 carbon atoms, and alkynyl groups having 2 to 6 carbon atoms.

The alkyl groups having 1 to 6 carbon atoms may be linear, branched, or cyclic, and examples thereof include methyl, ethyl, n-propyl, isopropyl, n-butyl, isobutyl, sec-butyl, tert-butyl, n-pentyl, isopentyl, neopentyl, tert-pentyl, n-hexyl, cyclopropyl, cyclobutyl, cyclopentyl, and cyclohexyl groups.

The alkenyl groups having 2 to 6 carbon atoms may be linear, branched, or cyclic, and examples thereof include vinyl, allyl, methylvinyl, butenyl, pentenyl, hexenyl, cyclopropenyl, cyclobutenyl, cyclopentenyl, and cyclohexenyl groups.

The alkynyl groups having 2 to 6 carbon atoms may be linear, branched, or cyclic, examples thereof include ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, 1-hexynyl, 2-hexynyl, 1-ethyl-2-butynyl, 3-hexynyl, 1-methyl-2-pentynyl, 1-methyl-3-pentynyl, 4-methyl-1-pentynyl, 3-methyl-1-pentynyl, 5-hexynyl, and 1-ethyl-3-butynyl groups.

Specific examples of the silane coupling agent (a) represented by the above general formula (1) include 8-methacryloyloxyoctyltrimethoxysilane, 9-methacryloyloxynonyltrimethoxysilane, 10-methacryloyloxydecyltrimethoxysilane, 11-methacryloyloxyundecyltrimethoxysilane, 11-methacryloyloxyundecyldichloromethylsilane, 11-methacryloyloxyundecyltrichlorosilane, 11-methacryloyloxyundecyldimethoxymethylsilane, 12-methacryloyloxydodecyltrimethoxysilane, and 13-methacryloyloxytridecyltrimethoxysilane. These may be used alone or two or more thereof may be used in combination as appropriate. Among these, 8-methacryloyloxyoctyltrimethoxysilane, 9-methacryloyloxynonyltrimethoxysilane, 10-methacryloyloxydecyltrimethoxysilane, and 11-methacryloyloxyundecyltrimethoxysilane are preferable in terms of ease of both achieving a higher content of the irregularly-shaped inorganic particles (B) having an average particle diameter of 0.1 to 0.3 μm in the composition and obtaining a paste with a consistency of 25 to 55 suitable for use as a flowable composite resin. More preferred is 11-methacryloyloxyundecyltrimethoxysilane.

The method for surface-treating the inorganic particles with a silane coupling agent is not particularly limited, as long as the method is one that allows the silane coupling agent to be adsorbed on the surfaces of the inorganic particles. Examples include: a method in which the inorganic particles that are being stirred in a mixing chamber are sprayed with a solution of a silane coupling agent diluted with a solvent, and then are dried by heating under continuous stirring in the chamber for a certain period of time; and a method in which the inorganic particles and the silane coupling agent are stirred and mixed in a solvent, followed by heat drying.

The amount of the silane coupling agent (a) for treating the irregularly-shaped inorganic particles (B) is preferably 0.5 to 15 parts by weight, and more preferably 1 to 13 parts by weight relative to 100 parts by weight of the irregularly-shaped inorganic particles (B) that have yet to be treated. If the amount is less than 0.5 parts by weight, the surface treatment may be insufficient, and the resulting inorganic particles may be only those having low hydrophobicity. If the amount is more than 15 parts by weight, the excess of the silane coupling agent may form an oligomer and interfere with the surface treatment.

The refractive index of the irregularly-shaped inorganic particles (B) is preferably 1.52 to 1.58. If the refractive index is less than 1.52 or more than 1.58, the difference in refractive index from the polymer of the polymerizable monomer (A) is likely to be large, which may lead to a situation where the cured product of the composition is white and opaque and lacks transparency close to that of natural teeth. In terms of ease of reducing the difference in refractive index from the polymerizable monomer (A), the refractive index of the irregularly-shaped inorganic particles (B) is more preferably 1.525 to 1.58, and even more preferably 1.53 to 1.58. In addition, the absolute value of the difference between the refractive index after polymerization of the polymerizable monomer (A) and the refractive index of the irregularly-shaped inorganic particles (B) is preferably 0.03 or less. In this case, particularly excellent transparency is obtained.

Any irregularly-shaped inorganic particles having an average particle diameter of 0.1 to 0.3 μm can be used as the irregularly-shaped inorganic particles (B) without any other limitation. Examples of the inorganic particles include particles of various types of glass materials (materials containing silica as a main component and containing an oxide of a heavy metal, boron, or aluminum as necessary, and examples thereof include dental glass powders such as E glass, barium glass (GM 27884 and 8235 manufactured by Schott AG, E 2000 and E 3000 manufactured by ESSTECH, Inc.), and lanthanum glass-ceramics (GM 31684 manufactured by Schott AG)); various types of ceramics; composite oxides such as silica-titania and silica-zirconia; kaolin; clay minerals (such as montmorillonite); mica; ytterbium fluoride; and yttrium fluoride. Each of these may be used alone, or two or more thereof may be used as a mixture. Among the above-mentioned inorganic particles, inorganic particles containing silica as a main component are preferably used as the irregularly-shaped inorganic particles (B) in the dental curable composition of the present invention.

Inorganic Ultrafine Particles (C)

The inorganic ultrafine particles (C) used in the present invention are inorganic ultrafine particles surface-treated with the silane coupling agent (b) represented by a formula that is the same as the formula (1) representing the silane coupling agent (a) except that q is an integer of 1 to 6. Their average particle diameter is 5 to 50 nm.

The average particle diameter is preferably 10 to 40 nm. The average particle diameter of the inorganic ultrafine particles (C) can be measured by taking an electron microscope photograph of the ultrafine particles and calculating the average of the particle diameters of randomly-selected 100 ultrafine particles. When the ultrafine particles are non-spherical, the particle diameter of each ultrafine particle is defined as an arithmetic average of the maximum and minimum lengths of the ultrafine particle.

For the dental curable composition of the present invention, the irregularly-shaped inorganic particles (B) having an average particle diameter of 0.1 to 0.3 μm are surface-treated with the silane coupling agent (a) having a long alkyl chain so as to increase the hydrophobicity of the surfaces of the irregularly-shaped inorganic particles (B), and therefore the filler content can be increased, with the result that high mechanical strength of the cured product of the composition and appropriate consistency of the paste of the composition are obtained. However, the use of the irregularly-shaped inorganic particles (B) alone cannot provide sufficient formability and handling properties for use as a flowable composite resin. In the present invention, therefore, the inorganic ultrafine particles (C) treated with another particular silane coupling agent are further used as an adjuster of the properties of the paste of the composition to impart appropriate thixotropy. Thus, a paste composition can be obtained that exhibits formability and handling properties appropriate for use as a flowable composite resin while having consistency appropriate for use as a flowable composite resin.

In the present invention, since a large amount of the irregularly-shaped inorganic particles (B) are contained to achieve high polishability and gloss retention, a small amount of the inorganic ultrafine particles (C) need to exert an adequate function as a thickener. When the irregularly-shaped inorganic particles (B) are surface-treated with the silane coupling agent (a), the addition of a small amount of the inorganic ultrafine particles (C) cannot provide appropriate formability because, due to having an increased hydrophobicity comparable to that of the polymerizable monomer or the irregularly-shaped inorganic particles (B) subjected to the particular surface treatment described above, the inorganic ultrafine particles (C) easily blend with the monomer or the inorganic particles (B). In addition, if the inorganic ultrafine particles (C) that have not been surface-treated are used, the inorganic ultrafine particles (C), due to their significantly reduced affinity for the polymerizable monomer and the inorganic ultrafine particles (C), are separated and settle down after the composition is left for a long period of time, which means that it is difficult to obtain a stable composition.

In view of the above facts, the present invention uses the silane coupling agent (b) for treatment of the surfaces of the inorganic ultrafine particles (C) so that the surfaces have appropriate hydrophobicity, thus making it possible to impart an appropriate level of formability to the composition and prepare the composition having excellent shape retention even by the addition of a small amount of the inorganic particles (C).

The silane coupling agent (b) has a structure represented by a formula that is the same as the above formula (1) representing the silane coupling agent (a), except that q is an integer of 1 to 6. Insofar as $R^1$, $R^2$, $R^3$, and p in the silane coupling agent (b) fall within the definition of $R^1$, $R^2$, $R^3$, and p in the formula (1), $R^1$, $R^2$, $R^3$, and p in the silane coupling agent (b) may be the same as or different from $R^1$, $R^2$, $R^3$, and p in the silane coupling agent (a). Specific examples of the silane coupling agent (b) include methacryloyloxymethyltrimethoxysilane, 2-methacryloyloxyethyltrimethoxysilane, 3-methacryloyloxypropyltrimethoxysilane, 4-methacryloyloxybutyltrimethoxysilane, 5-methacryloyloxypentyltrimethoxysilane, and 6-methacryloyloxyhexyltrimethoxysilane. These may be used alone or two or more thereof may be used in combination as appropriate. Among these, methacryloyloxymethyltrimethoxysilane, 2-methacryloyloxyethyltrimethoxysilane, 3-methacryloyloxypropyltrimethoxysilane, and 4-methacryloyloxybutyltrimethoxysilane are preferable in terms of imparting an appropriate level of shape retention. More preferred is 3-methacryloyloxypropyltrimethoxysilane.

Commonly-known inorganic ultrafine particles used in dental curable compositions etc. are used as the inorganic ultrafine particles (C) without any limitation. Preferred examples include: particles of inorganic oxides such as silica, alumina, titania, and zirconia or composite oxides thereof, and particles of calcium phosphate, hydroxylapatite, yttrium fluoride, ytterbium fluoride, barium titanate, and potassium titanate. Preferred are particles of silica, alumina, titania, silica-alumina composite oxide, and silica-zirconia composite oxide which are prepared by flame pyrolysis, and examples thereof include those manufactured by Nippon Aerosil Co., Ltd. under the trade names Aerosil, Aerosil 130, Aerosil 380, Aerosil OX-50, Aeroxide AluC, Aeroxide $TiO_2P25$, Aeroxide $TiO_2P25S$, VP Zirconium Oxide 3-YSZ, and VP Zirconium Oxide 3-YSZ PH. The shape of the inorganic ultrafine particles (C) is not particularly limited, and can be selected as appropriate.

In the present invention, the inorganic ultrafine particles (C) can be suitably used also in the form of agglomerated particles each formed by agglomeration of the inorganic ultrafine particles (C). Particularly, when the particle diameter of the agglomerated particles is in the range of 1 to 10 μm, a dental curable composition having excellent mechanical strength and excellent aesthetic quality can be obtained. Thus, in another preferred embodiment of the present invention, the dental curable composition contains agglomerated particles each of which is composed of the inorganic ultrafine particles (C) as primary particles having an average (primary) particle diameter of 5 to 50 nm and which have an average secondary particle diameter of 1 to 10 μm. The average particle diameter of the agglomerated particles can be determined by laser diffraction scattering. Specifically, for example, the average particle diameter can be measured using a laser diffraction particle size analyzer (SALD-2100 manufactured by Shimadzu Corporation) and using a 0.2% aqueous sodium hexametaphosphate solution as a dispersion medium.

When the inorganic ultrafine particles (C) form agglomerated particles, the average particle diameter of the inorganic ultrafine particles (C) is preferably 5 to 35 nm, and more preferably 7 to 20 nm, in terms of ease of increasing the number of interfaces with the polymerizable monomer (A) which serve as sites for refraction and scattering of light and ease of obtaining agglomerates having an appropriate strength. The average particle diameter of the agglomerates of the inorganic ultrafine particles (C) is preferably 1 to 10 μm, more preferably 1 to 8 μm, and even more preferably 1.2 to 5 μm. If the average particle diameter is less than 1 μm, the agglomerates' function of adjusting transmitted light is deteriorated, and accordingly their amount to be added has to be increased, which may result in a deterioration in light diffusion property and transparency of the cured product of the composition. If the average particle diameter is more than 10 μm, the transparency of the cured product may be deteriorated due to increase in the degree of light refraction or scattering. Additionally, even if the agglomerates have an average primary particle diameter of 5 to 50 nm, the polishability (particularly the ease of polishing) may be deteriorated.

Commercially-available inorganic ultrafine particles are usually present in the form of agglomerates; however, they have only such a weak agglomeration force that when 10 mg of a powder consisting of the inorganic ultrafine particles is put into 300 mL of water or 300 mL of water to which has been added 5 weight % or less of a surfactant such as sodium hexametaphosphate (the water serves as a dispersion medium), and is subjected to dispersion treatment using an ultrasonic wave output with a power of 40 W at a frequency of 39 KHz for 30 minutes, the agglomerates are separated into particles having diameters indicated by the maker. By contrast, the agglomerated particles in the present invention are those in which the primary particles are agglomerated together so strongly that they are hardly separated from each other even when exposed to the above conditions.

A method suitably used for producing strongly-agglomerated particles from commercially-available inorganic ultrafine particles is one in which, in order to enhance the agglomeration force, the inorganic ultrafine particles are heated to a temperature very close to that at which they melt, so that the inorganic ultrafine particles in contact with each other are slightly fused together. In this case, in order to control the shape of the agglomerated particles, the inorganic ultrafine particles may be processed into agglomerated form before heating. Examples of such a method include those in which the inorganic ultrafine particles are put into a proper container and subjected to a pressure or in which the inorganic ultrafine particles are dissolved in a solvent, and the solvent is finally removed by a technique such as spray drying.

A still another suitable method for fabricating agglomerates of the inorganic ultrafine particles is one which uses a silica sol, an alumina sol, a titania sol, a zirconia sol, or the like fabricated by a wet process and in which the sol is dried by a technique such as freeze drying or spray drying, followed by heat treatment as necessary. With this method, agglomerated particles each composed of primary particles strongly agglomerated together can easily be obtained. Specific examples of the sol include those manufactured by NIPPON SHOKUBAI CO., LTD. under the trade name SEAHOSTAR, those manufactured by JGC Catalysts and Chemicals Ltd. under the trade names OSCAL and QUEEN TITANIC, and those manufactured by Nissan Chemical Industries, Ltd. under the trade names SNOWTEX, ALUMINASOL, CELNAX, and NANOUSE. The shape of the inorganic ultrafine particles is not particularly limited, and can be selected as appropriate. Alternatively, commercially-available agglomerates of inorganic ultrafine particles may be used as such. Examples thereof include SILICA MICRO BEAD P500 (manufactured by JGC Catalysts and Chemicals Ltd.) and SILICA MICRO BEAD P1500 (manufactured by JGC Catalysts and Chemicals Ltd.).

There is no particular limitation on the specific surface area and pore volume of the agglomerated particles of the inorganic ultrafine particles (C). In terms of ease of obtaining a desired level of light diffusion property and transparency of the cured product of the composition, it is preferable that the specific surface area be 50 to 400 $m^2/g$ and the pore volume be 0.05 to 1.5 mL/g. It is more preferable that the specific surface area be 50 to 300 $m^2/g$ and the pore volume be 0.1 to 1.0 mL/g. It is particularly preferable that the specific surface area be 80 to 250 $m^2/g$ and the pore volume be 0.15 to 0.5 mL/g.

The inorganic ultrafine particles (C) used in the present invention preferably have a refractive index of 1.43 to 1.50. If the refractive index of the inorganic ultrafine particles (C) is less than 1.43, the difference in refractive index from the polymer of the polymerizable monomer (A) and the irregularly-shaped inorganic particles (B) will be too large, and therefore sufficient transparency may not be obtained. If the refractive index of the inorganic ultrafine particles (C) is more than 1.50, the difference in refractive index from the polymer of the polymerizable monomer (A) and the irregularly-shaped inorganic particles (B) will be too small, and therefore sufficient light diffusion property may not be obtained. In terms of ease of increasing the difference in refractive index from the polymer of the polymerizable monomer (A) and the irregularly-shaped inorganic particles (B), the refractive index of the inorganic ultrafine particles (C) is preferably 1.43 to 1.48, and more preferably 1.43 to 1.46. When the inorganic ultrafine particles (C) are present in the form of agglomerated particles, the refractive index of the agglomerated particles is preferably within the above-specified range. The difference {(A)–(C)} between the refractive index after polymerization of the polymerizable monomer (A) and the refractive index of the inorganic ultrafine particles (C) (or the refractive index of agglomerated particles when the inorganic ultrafine particles (C) are present in the form of the agglomerated particles) is preferably 0.05 or more. In this case, particularly excellent light diffusion property is obtained.

The light diffusion property refers to the property of a translucent material such as a dental composite material to refract or reflect light incident on the material by the action of the filler contained in the material so that the light is diffused in various directions. The reflected and diffused light to be observed have a color reflecting the color tone or background color of the dental composite material. It is therefore thought that the higher the light diffusing property, the greater the effect of blurring the background color of a restorative material or blurring the boundary between the restorative material and a natural tooth, and accordingly the higher the conformity with the color tone of the natural tooth. A proposed index of the light diffusion property is the degree of diffusion D defined by the following formula (2).

$$D=(I_{20}/\cos 20°+I_{70}/\cos 70°/(2I_0) \tag{2}$$

(In the formula, I represents the luminance of light transmitted through a sample, and $I_0$, $I_{20}$, and $I_{70}$ respectively represent the luminances (the light intensities) in directions forming angles of 0°, 20°, and 70° with the direction perpendicular to the sample sheet (the direction of incident light)).

The measurement of these luminances (light intensities) can be performed using a variable angle photometer or a goniophotometer. A higher value of the degree of diffusion D indicates that the cured product has higher light diffusing property.

For the dental curable composition of the present invention, a value of the degree of diffusion D that is 0.01 to 0.5 can be achieved. If the value of the degree of diffusion D is less than 0.01, this means that the light diffusion property of the dental curable composition is insufficient, and good conformity with a natural tooth is difficult to obtain. If the value is more than 0.5, this means that the light diffusion property is too high, and sufficient transparency is not obtained. That is, the dental curable composition of the present invention can have light diffusion property appropriately high for obtaining good conformity with a natural tooth. In terms of the conformity with a natural tooth, the value of the degree of diffusion D is preferably 0.02 to 0.45, and more preferably 0.03 to 0.42. For the dental curable composition of the present invention, the degree of diffusion D can be set within the preferable ranges by adjusting the above-mentioned difference in refractive index. There is a tendency that the smaller the difference in refractive index, the smaller the degree of diffusion D.

The amount of the silane coupling agent (b) for treating the inorganic ultrafine particles (C) may be adjusted as appropriate in consideration of, for example, the average particle diameter of the inorganic particles used. The amount is preferably is 1 to 20 parts by weight relative to 100 parts by weight of the inorganic ultrafine particles (C) that have yet to be treated. When the inorganic ultrafine particles (C) are present in the form of agglomerated particles, each of the inorganic ultrafine particles (C) as primary particles may be treated with the silane coupling agent (b), or the agglomerated particles may be treated with the silane coupling agent (b).

Relative to the amount of total inorganic particles, the content of the irregularly-shaped inorganic particles (B) is 92.5 to 98 weight %, and the content of the inorganic ultrafine particles (C) is 2 to 7.5 weight %. If the content of the irregularly-shaped inorganic particles (B) is less than 92.5 weight % (or if the content of the inorganic ultrafine particles (C) is more than 7.5 weight %), a paste with a consistency suitable for use as a flowable composite resin will not be obtained. In addition, a situation may arise where the paste cannot be extruded when discharged from a syringe through a needle due to too high a discharge force. Furthermore, the mechanical strength may be reduced. If the content of the irregularly-shaped inorganic particles (B) is more than 98 weight % (or if the content of the inorganic ultrafine particles (C) is less than 2 weight %), the resulting paste will have poor formability and be runny; that is, a paste having good handling properties for use as a flowable composite resin will not be obtained. Furthermore, the mechanical strength may be reduced.

The dental curable composition of the present invention has a consistency of 25 to 55 so that it can be used particularly as a flowable composite resin. The term "consistency" as used herein refers to a value determined by pressing 0.5 mL of a paste with a load of 40 g at 25° C. for 120 seconds, measuring the then longest and shortest diameters of the paste, and calculating the arithmetic average of the two diameters. The consistency is preferably 27 to 45, and more preferably 29 to 40. If the consistency is less than 25, this means that the paste has too low a consistency which, when the paste is discharged from a syringe through a needle, causes too high a discharge force and thereby poor discharge performance. In addition, if the consistency is more than 55, the resulting paste will be runny; that is, a paste having good handling properties for use as a flowable composite resin will not be obtained.

The dental curable composition of the present invention may contain inorganic particles other than the irregularly-shaped inorganic particles (B) and the inorganic ultrafine particles (C), to the extent that the effect of the present invention is not impaired.

In order to facilitate polymerization and curing, the dental curable composition of the present invention may contain a polymerization initiator. A commonly-known polymerization initiator can be used, and the polymerization initiator is selected usually in consideration of the polymerizability of the polymerizable monomer and the polymerization conditions.

For polymerization at room temperature, redox initiator systems such as organic peroxide/amine systems and organic peroxide/amine/sulfinic acid (or a salt thereof) systems are suitably used. In the case of using a redox initiator system, it is necessary that the oxidant and the reductant be separately packaged, and they be mixed together immediately before use. Examples of the oxidant include organic peroxides such as diacyl peroxides, peroxyesters, peroxycarbonates, dialkyl peroxides, peroxyketals, ketone peroxides, and hydroperoxides. Specifically, examples of the diacyl peroxides include benzoyl peroxide, 2,4-dichlorobenzoyl peroxide, m-toluoyl peroxide, and lauroyl peroxide. Examples of the peroxyesters include t-butyl peroxybenzoate, bis-t-butyl peroxyisophthalate, and t-butyl peroxy-2-ethylhexanoate. Examples of the peroxycarbonates include t-butyl peroxy isopropyl carbonate. Examples of the dialkyl peroxides include dicumyl peroxide, di-t-butyl peroxide, and 2,5-dimethyl-2,5-bis(benzoylperoxy)hexane. Examples of the peroxyketals include 1,1-bis(t-butylperoxy)3,3,5-trimethylcyclohexane. Examples of the ketone peroxides include methyl ethyl ketone peroxide. Examples of the hydroperoxides include t-butyl hydroperoxide. A reductant usually used is a tertiary amine, and examples thereof include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-i-propylaniline, N,N-dimethyl-4-t-butylaniline, N,N-dimethyl-3,5-di-t-butylaniline, N,N-bis(2-hydroxyethyl)-p-toluidine, N,N-bis(2-hydroxyethyl)-3,5-dimethylaniline, N,N-bis(2-hydroxyethyl)-3,4-dimethylaniline, N,N-bis(2-hydroxyethyl)-4-ethylaniline, N,N-bis(2-hydroxyethyl)-4-i-propylaniline, N,N-bis(2-hydroxyethyl)-4-t-butylaniline, N,N-bis(2-hydroxyethyl)-3,5-di-i-propylaniline, N,N-bis(2-hydroxyethyl)-3,5-di-t-butylaniline, ethyl 4-dimethylaminobenzoate, n-butoxyethyl 4-dimethylaminobenzoate, (2-methacryloyloxy)ethyl 4-dimethylaminobenzoate, trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate. As well as the above initiator systems, oxidation-reduction initiator systems such as cumenehydroperxide/thiourea systems, ascorbic acid/$Cu^{2+}$ salt systems, and organic sulfinic acid (or salt thereof)/amine/inorganic peroxide systems can be suitably used, and tributylborane, organic sulfinic acid, etc. can also be suitably used.

For photopolymerization by visible light irradiation, oxidation-reduction initiator systems such as α-diketone/tertiary amine systems, α-diketone/aldehyde systems, and α-diketone/mercaptan systems are preferable. Examples of photopolymerization initiator systems include α-diketone/ reductant systems, ketal/reductant systems, and thioxanthone/reductant systems. Examples of the α-diketone include camphorquinone, benzyl, and 2,3-pentanedione. Examples of the ketal include benzyl dimethyl ketal and benzyl diethyl ketal. Examples of the thioxanthone include 2-chlorothioxanthone and 2,4-diethylthioxantone. Examples of the reductant include: Michler's ketone; tertiary amines such as 2-(dimethylamino)ethyl methacrylate, N,N-bis [(meth)acryloyloxyethyl]-N-methylamine, ethyl N,N-dimethylaminobenzoate, butyl 4-dimethylaminobenzoate, butoxyethyl 4-dimethylaminobenzoate, N-methyldiethanolamine, 4-dimethylaminobenzophenone, N,N-bis(2-hydroxyethyl)-p-toluidine, and dimethylaminophenanthrol; aldehydes such as citronellal, lauryl aldehyde, phthaldialdehyde, dimethylaminobenzaldehyde, and terephthalaldehyde; and compounds having a thiol group, such as 2-mercaptobenzoxazole, decanethiol, 3-mercaptopropyltrimethoxysilane, 4-mercaptoacetophenone, thiosalicylic acid, and thiobenzoic acid. An α-diketone/organic peroxide/reductant system prepared by adding an organic peroxide to any of the above-mentioned oxidation-reduction initiator systems can also be suitably used.

For photopolymerization by ultraviolet irradiation, benzoin alkyl ethers, benzyl dimethyl ketals and the like are suitable. Furthermore, photopolymerization initiators based on an acylphosphine oxide or a bisacylphosphine oxide can also be suitably used. Examples of such an acylphosphine oxide include 2,4,6-trimethylbenzoyldiphenylphosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl di-(2,6-dimethylphenyl)phosphonate, and 2,4,6-trimethylbenzoylethoxyphenylphosphine oxide. Examples of the bisacylphosphine oxide include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl) phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, and bis(2,4,6-trimethylbenzoy)phenylphosphine oxide. Furthermore, these (bis)acylphosphine oxides may contain a water-soluble substituent. The photopolymerization initiators based on these (bis)acylphosphine oxides can be used alone, and can be used also in combination with reductants such as amines, aldehydes, mercaptans, and sulfinic acid salts. Combinations with the above-mentioned initiators for visible light photopolymerization can also be suitably used.

The above-mentioned polymerization initiators may be used alone or two or more thereof may be used in combination as appropriate. The content of the total polymerization initiator is preferably 0.1 to 10 parts by weight, and more preferably 0.2 to 5.0 parts by weight relative to 100 parts by weight of the amount of the total polymerizable monomer.

In the dental curable composition of the present invention, there may be contained an additive such as a polymerization inhibitor, an ultraviolet absorber, a fluorescent agent, or a pigment in addition to the polymerizable monomer and inorganic particles.

Examples of the polymerization inhibitor include 3,5-dibutyl-4-hydroxytoluene, hydroquinone, dibutylhydroquinone, dibutylhydroquinone monomethyl ether, 2,6-t-butylphenol, and 4-methoxyphenol. One of these inhibitors, or two or more thereof, may be contained.

There is no other particular limitation on the dental curable composition of the present invention, as long as the composition contains the polymerizable monomer (A), a given amount of the irregularly-shaped inorganic particles (B), and a given amount of the inorganic ultrafine particles (C). The composition can easily be produced by a method well-known to persons skilled in the art in a form appropriate for the intended use (in one-paste form, in two-paste form, in powder-liquid form, or in molded form). When utilizing chemical polymerization function or polymerization initiation function for both chemical polymerization and photopolymerization, it is necessary that the composition containing an oxidant and the composition containing a reductant be separately packaged, and they be mixed together immediately before use.

The dental curable composition of the present invention, when in the form of a cured product, has excellent mechanical strength, polishability, and gloss retention, and, when in the form of a paste, has a consistency appropriate for discharge through a needle attached to the tip of a syringe and exhibits good formability and handling properties after discharge through the needle. Therefore, the dental curable composition of the present invention can be suitably used as a material for substituting for a part or the whole of a natural tooth in the field of dentistry, and is best suited as a flowable composite resin. In the filling operation in dental treatment, the dental curable composition of the present invention can be discharged through a needle having a small-diameter orifice and attached to the tip of a container (syringe-type container) holding the composition; that is, the composition can be directly injected from the syringe to fill a cavity. Since the filling operation can be done simply by feeding the composition from the syringe into the cavity, a reduction in treatment time can also be achieved.

When the dental curable composition of the present invention is provided as a dental flowable composite resin, it is provided, for example, in the form of a package including a container holding the flowable composite resin and a needle chip to be attached to the tip of the container. The container is composed, for example, of a tubular syringe and a plunger adapted to be inserted from the bottom of the syringe. The inner diameter of the needle of the needle chip is usually 0.3 to 0.9 mm. When the flowable composite resin is of the two-component type, the container may be composed, for example, of two syringes coupled in parallel and two plungers coupled in parallel, and a static mixer may be provided at the tip of each syringe.

EXAMPLES

Hereinafter, the present invention will be described in detail with reference to examples and comparative examples. However, the present invention is not limited to these examples.

[Average Particle Diameter of Inorganic Particles B]

The average particle diameter of the inorganic particles B was determined as a volume median particle diameter in a particle size distribution measured by laser diffraction scattering. The volume median diameter refers to a particle diameter at the point where the cumulative volume frequency in terms of volume fraction reaches 50% when calculated in order of increasing particle diameter.

Measuring instrument: SALD-2100 (manufactured by Shimadzu Corporation)

Analysis software: Light transmission centrifugal sedimentation

Dispersion medium: 0.2% sodium hexametaphosphate solution

Dispersion condition: Add 15 mg of a sample into 20 mL of the dispersion medium, and disperse the sample with an ultrasonic disperser for 30 minutes to prepare a sample dispersion.

Measurement condition: Perform measurement on the sample dispersion, and determine the proportions of the number of particles having a volume median diameter and the number of particles having a diameter of 0.01 to 100 μm.

[Refractive Index]

The measurement was performed with an Abbe refractometer by a liquid immersion method at 25° C., in which a sodium D-line was used as a light source, and liquids such as diiodomethane in which sulfur is dissolved, 1-bromonaphthalene, methyl salicylate, dimethylformamide, and 1-pentanol, or the like was used as a liquid.

[Average Particle Diameter of Inorganic Ultrafine Particles C]

Image analysis was performed on electron microscope photographs of 100 or more inorganic ultrafine particles using image analysis software (Mac-View manufactured by Mountech Co., Ltd.), and then a volume median particle diameter was calculated as the average particle diameter. When the inorganic ultrafine particles C were in the form of agglomerated particles, the particle diameter of the agglomerated particles was determined in the same manner as for the average particle diameter of the inorganic particles B.

Production Example 1 of Inorganic Particles

Into a three-neck flask were put 100 g of barium glass "GM27884NanoFine180 (Average particle diameter=0.18 μm, Refractive index=1.53)" (manufactured by Schott AG), 11 g of 11-methacryloyloxyundecyltrimethoxysilane, and 200 mL of toluene, followed by stirring at room temperature for 2 hours. The toluene was distilled away under reduced pressure, followed by vacuum drying at 40° C. for 16 hours and then by heating at 90° C. for 3 hours. Thus, inorganic particles (b-1) provided with surface-treated layers and having an average particle diameter of 0.18 μm were obtained.

Production Example 2 of Inorganic Particles

Into a three-neck flask were put 100 g of barium glass "GM27884NanoFine 180 (Average particle diameter=0.18 μm, Refractive index=1.53)" (manufactured by Schott AG), 11 g of 8-methacryloyloxyoctyltrimethoxysilane, and 200 mL of toluene, followed by stirring at room temperature for 2 hours. The toluene was distilled away under reduced pressure, followed by vacuum drying at 40° C. for 16 hours and then by heating at 90° C. for 3 hours. Thus, inorganic particles (b-2) provided with surface-treated layers and having an average particle diameter of 0.18 μm were obtained.

Production Example 3 of Inorganic Particles

Into a three-neck flask were put 100 g of barium glass "GM27884NanoFine180 (Average particle diameter=0.18 μm, Refractive index=1.53)" (manufactured by Schott AG), 11 g of 13-methacryloyloxytridecyltrimethoxysilane, and 200 mL of toluene, followed by stirring at room temperature for 2 hours. The toluene was distilled away under reduced pressure, followed by vacuum drying at 40° C. for 16 hours and then by heating at 90° C. for 3 hours. Thus, inorganic particles (b-3) provided with surface-treated layers and having an average particle diameter of 0.18 μm were obtained.

Production Example 4 of Inorganic Particles

Into a three-neck flask were put 100 g of barium glass "GM27884 (Average particle diameter=0.10 μm, Refractive index=1.53)" (manufactured by Schott AG), 11 g of 13-methacryloyloxytridecyltrimethoxysilane, and 200 mL of toluene, followed by stirring at room temperature for 2 hours. The toluene was distilled away under reduced pressure, followed by vacuum drying at 40° C. for 16 hours and then by heating at 90° C. for 3 hours. Thus, inorganic particles (b-4) provided with surface-treated layers and having an average particle diameter of 0.10 μm were obtained.

Production Example 5 of Inorganic Particles

Into a three-neck flask were put 100 g of barium glass "GM27884 UF0.4 (Average particle diameter=0.4 μm, Refractive index=1.53)" (manufactured by Schott AG), 7.0 g of 11-methacryloyloxyundecyltrimethoxysilane, and 200 mL of toluene, followed by stirring at room temperature for 2 hours. The toluene was distilled away under reduced pressure, followed by vacuum drying at 40° C. for 16 hours and then by heating at 90° C. for 3 hours. Thus, inorganic particles (b-5) provided with surface-treated layers and having an average particle diameter of 0.4 μm were obtained.

Production Example 6 of Inorganic Particles

Into a three-neck flask were put 100 g of barium glass "GM27884NanoFine 180 (Average particle diameter=0.18 μm, Refractive index=1.53)" (manufactured by Schott AG), 11 g of 3-methacryloyloxypropyltrimethoxysilane, and 200 mL of toluene, followed by stirring at room temperature for 2 hours. The toluene was distilled away under reduced pressure, followed by vacuum drying at 40° C. for 16 hours and then by heating at 90° C. for 3 hours. Thus, inorganic particles (b-6) provided with surface-treated layers and having an average particle diameter of 0.18 μm were obtained.

Production Example 7 of Inorganic Particles

Into a three-neck flask were put 100 g of agglomerated silica, "SILICA MICRO BEAD P-500" (Average particle diameter of ultrafine particles=12 nm, Average particle diameter of agglomerates=2 μm)" (manufactured by JGC Catalysts and Chemicals Ltd.), 20 g of 3-methacryloxypropyltrimethoxysilane, and 200 mL of toluene, followed by stirring at room temperature for 2 hours. The toluene was distilled away under reduced pressure, followed by vacuum drying at 40° C. for 16 hours and then by heating at 90° C. for 3 hours. Thus, silane-treated inorganic particles (c-1) having an average particle diameter of 1.6 μm, a refractive index of 1.44, a specific surface area of 99 $m^2/g$, and a pore volume of 0.19 mL/g were obtained.

Production Example 8 of Inorganic Particles

A silica sol, SNOWTEX ST-20 (Average particle diameter=14 nm) manufactured by Nissan Chemical Industries, Ltd., was predried by spray drying using a micro mist spray dryer "MDL-050" (manufactured by Fujisaki Electric Co., Ltd.) under conditions where the inlet temperature was 200° C., the internal temperature was 80° C., the air flow rate was 30 mL/min, and the liquid flow rate was 15 mL/min. The resulting spherical powder was sintered with an electric furnace set at 400° C. for 1 hour, and a sintered powder was obtained. Into a three-neck flask were put 100 g of the obtained powder, 20 g of 3-methacryloxypropyltrimethoxysilane, and 200 mL of toluene, followed by stirring at room temperature for 2 hours. The toluene was distilled away under reduced pressure, followed by vacuum drying at 40° C. for 16 hours and then by heating at 90° C. for 3 hours. Thus, silane-treated inorganic particles (c-2) having an average particle diameter of 4.9 µm, a refractive index of 1.45, a specific surface area of 110 m²/g, and a pore volume of 0.17 mL/g were obtained.

Production Example 9 of Inorganic Particles

Into a three-neck flask were put 100 g of inorganic ultrafine particles having an average particle diameter of 20 nm, Aerosil 130 (Refractive index=1.45, manufactured by Nippon Aerosil Co., Ltd.), 40 g of 3-methacryloxypropyltrimethoxysilane, and 200 mL of toluene, followed by stirring at room temperature for 2 hours. The toluene was distilled away under reduced pressure, followed by vacuum drying at 40° C. for 16 hours and then by heating at 90° C. for 3 hours. Thus, inorganic ultrafine particles (c-3) provided with surface-treated layers were obtained.

Production Example 10 of Inorganic Particles

Into a three-neck flask were put 100 g of fine particles of an inorganic filler having an average particle diameter of 40 nm (Refractive index=1.45, manufactured by Nippon Aerosil Co., Ltd. under the trade name Aerosil OX-50), 40 g of 3-methacryloyloxypropyltrimethoxysilane, and 600 mL of toluene, followed by vigorous stirring at 30° C. for 20 minutes. The toluene was distilled away at 30° C. under reduced pressure, followed by vacuum drying at 40° C. for 16 hours. Thus, inorganic particles (c-4) provided with surface-treated layers were obtained.

Production Example 11 of Inorganic Particles

Into a three-neck flask were put 100 g of fine particles of an inorganic filler having an average particle diameter of 7 nm (Refractive index=1.45, manufactured by Nippon Aerosil Co., Ltd. under the trade name Aerosil 380), 40 g of 3-methacryloyloxypropyltrimethoxysilane, and 600 mL of toluene, followed by vigorous stirring at 30° C. for 20 minutes. The toluene was distilled away at 30° C. under reduced pressure, followed by vacuum drying at 40° C. for 16 hours. Thus, inorganic particles (c-5) provided with surface-treated layers were obtained.

Production Example 12 of Inorganic Particles

Into a three-neck flask were put 100 g of agglomerated silica, "SILICA MICRO BEAD P-500" (Average particle diameter of ultrafine particles=12 nm, Average particle diameter of agglomerates=2 µm, Refractive index=1.44)" (manufactured by JGC Catalysts and Chemicals Ltd.), 7.0 g of 11-methacryloyloxyundecyltrimethoxysilane, and 200 mL of toluene, followed by stirring at room temperature for 2 hours. The toluene was distilled away under reduced pressure, followed by vacuum drying at 40° C. for 16 hours and then by heating at 90° C. for 3 hours. Thus, inorganic particles (c-6) provided with surface-treated layers were obtained.

Production Example 13 of Inorganic Particles
(Production Method of Organic-Inorganic Composite Filler)

To 32 g of a polymerizable monomer mixture composed of 70 parts by weight of triethylene glycol dimethacrylate, 10 parts by weight of Bis-GMA, 20 parts by weight of neopentyl glycol dimethacrylate, and 0.5 parts by weight of benzoyl peroxide, there were added 68 g of the ultrafine filler particles (c-5), followed by mixing to achieve homogeneity. The composition obtained was cured by heating it in a nitrogen atmosphere at 100° C. for 24 hours, and the cured product was ground and classified to obtain an organic-inorganic composite filler (c-7) having an average particle diameter of 2 µm and a refractive index of 1.47.

Preparation Method for Examples 1 to 23 and Comparative Examples 1 to 6

With 100 parts by weight of the total amount of each polymerizable monomer mixture shown in Tables 1 to 4 were blended 0.20 parts by weight of camphorquinone, 0.30 parts by weight of ethyl N,N-dimethylaminobenzoate, 0.25 parts by weight of trimethyldiphenylphosphine oxide, and 0.05 parts by weight of dibutylhydroxytoluene (BHT). Thus, polymerizable monomer compositions were obtained. The abbreviations for the polymerizable monomers in the tables are as listed below.
D2.6E: 2,2-bis(4-methacryloyloxypolyethoxyphenynpropane
3G: Triethylene glycol dimethacrylate
Bis-GMA: 2,2-bis[4-(3-methacryloyloxy)-2-hydroxypropoxyphenyl]propane
DD: 1,10-decanediol dimethacrylate
NPG: Neopentyl glycol dimethacrylate
HD: 1,6-hexanediol dimethacrylate
UDMA: [2,2,4-trimethylhexamethylene bis(2-carbamoyloxyethyl)]dimethacrylate
U-4TH: N,N'-(2,2,4-trimethylhexamethylene)bis[2-(aminocarboxy)propane-1,3-diol]tetramethacrylate.

The irregularly-shaped inorganic particles (B) and the inorganic ultrafine particles (C) were added to the obtained polymerizable monomer composition, followed by mixing to achieve homogeneity. The homogeneous mixture was defoamed under vacuum. Thus, dental curable compositions in paste form of Examples 1 to 23 and Comparative Examples 1 to 6 shown in Tables 1 to 4 were prepared. The following tests for characteristic evaluation were performed on the prepared dental curable compositions. The results are shown in Tables 1 to 4.

Test Example 1 (Polishability)

Each of the prepared dental curable compositions was loaded into a Teflon mold (having a diameter of 10 mm and a thickness of 2.0 mm). Glass slides were pressed against the upper and lower surfaces of the composition, and only the upper side was irradiated with light using a dental visible light irradiation device (Pencure 2000 manufactured by Morita Corporation) for 10 seconds so as to cure the composition. The specimen was taken out of the Teflon mold, and its clean, smooth surface was polished with #600 abrasive paper under dry conditions. Then, using Volvere RX (manufactured by NSK Ltd.) as a processing engine and using Brown Silicone Points (manufactured by SHOFU INC.), the surface was further polished under flowing water conditions at a rotation speed of about 5000 rpm for 10 seconds, following which the surface was polished using Blue Silicone Points (manufactured by SHOFU INC.) at a rotation speed about 5000 rpm for 10 seconds. Thereafter, the gloss of the polished surface was measured using a glossmeter (VG-2000 manufactured by NIPPON DENSHOKU INDUSTRIES CO., LTD., Measurement angle=60 degrees), and was expressed as the ratio (gloss value) to the gloss of a mirror that was defined as 100. A gloss value of 65 or more is favorable, and a gloss value of 70 or more is more favorable.

Test Example 2 (Gloss Retention)

Each of the prepared dental curable compositions was loaded into a Teflon mold (having a diameter of 10 mm and a thickness of 2.0 mm). Glass slides were pressed against the upper and lower surfaces of the composition, and only the upper side was irradiated with light using a dental visible light irradiation device (Pencure 2000 manufactured by Morita Corporation) for 10 seconds so as to cure the composition. The specimen was taken out of the Teflon mold, and its clean, smooth surface was polished with #1500 abrasive paper, then with #2000 abrasive paper, and then with #3000 abrasive paper under dry conditions. The surface was polished finally with a diamond paste until a gloss value of 90 was reached. The thus fabricated specimen was subjected to a toothbrush abrasion test (Toothbrush: Between manufactured by Lion Corporation (Hardness of Bristles: Regular), Toothpaste: Dentor Clear MAX (manufactured by Lion Corporation), Load: 250 g, Test solution: Solution (50 mL) of 90 wt % of distilled water and 10 wt % of toothpaste, Number of abrasion cycles: 40,000), after which the gloss value of the specimen was measured. When the residual gloss value is 60 or more, the gloss retention is favorable, and when the residual gloss value is 65 or more, the gloss retention is more favorable.

Test Example 3 (Consistency)

Each of the prepared dental curable compositions was defoamed under vacuum, then loaded into a syringe, and allowed to stand at 25° C. for 2 hours. The thus prepared sample was used as a sample for consistency test. An amount of 0.5 mL of the sample was weighed out, and placed in a mound-like shape on the center of a glass sheet (5 cm×5 cm) in a thermostatic chamber set at 25° C. (humidity=40%). A 40 g glass sheet (5 cm×5 cm) was placed on the sample, and after 120 seconds, the longest diameter and shortest diameter of the sample were measured over the glass sheet. The arithmetic average of the two diameters was calculated and defined as the consistency. The longest diameter of the sample refers to the longest one of the diameters passing through the center of the sample, and the shortest diameter of the sample refers to one of the diameters passing through the center of the sample that is orthogonal to the longest diameter.

Test Example 4 (Discharge Force)

The discharge force measurement was performed using: a storage container composed of a polyolefin resin-made syringe (container for CLEARFIL MAJESTY LV having an inner diameter of 8 mm and a length of 63 mm) and a cylindrical plunger fitted to the syringe through the bottom of the syringe; and a needle chip attached to the tip of the syringe (20 G×½", the needle portion has an inner diameter of 0.65 mm and a length of 19 mm and is bent at an angle of 45° at a point 8.5 mm away from the tip). The members composing the storage container are opaque to environmental light.

Each of the prepared dental curable compositions (pastes) was defoamed under vacuum, and then 1.5 ml of the paste was loaded into the syringe. The needle chip was attached to the tip of the syringe, and the plunger was pushed to discharge the paste through the tip of the needle chip. The then applied discharge force (force required to extrude the paste out of the syringe) was measured using a universal testing machine (manufactured by Shimadzu Corporation, Product code "AGI-100". The storage container was placed vertically upright, and a crosshead fitted with a jig for compressive strength test was lowered in the container at a rate of 4 mm/minute to apply a load to and discharge the paste. The then maximum load was defined as the discharge force. The discharge force measurement was performed at 25° C. When the discharge force is less than 35 N, easy discharge is possible and the discharge performance is good. When the discharge force is 35 N to 50 N, discharge is possible but the discharge performance is poor. When the discharge force is more than 50 N, discharge is difficult and the discharge performance is very poor.

Test Example 5 (Formability)

A circle of 4 mm diameter was drawn beforehand on a square glass sheet having dimensions of 30 mm×30 mm, and 0.03 g of the paste was discharged to the inside of the circle using the same storage container and needle chip as those used in the discharge force evaluation described above. The glass sheet was placed horizontally in a thermostat set at 37° C., and left in this state for 30 seconds, after which the shape of the paste was visually observed. The shape (formability) of the discharged paste was evaluated according to the evaluation criteria listed below. Products whose formability is rated as 2 to 4 are acceptable products. For pastes of the low-flow type which are somewhat hard, the rating 2 or 3 is preferable, and the rating 3 is more preferable. For pastes of the high-flow type which are somewhat soft, the rating 3 or 4 is preferable, and the rating 4 is more preferable.

[Evaluation Criteria of Formability]
1: A hemisphere is not formed, and the as-extruded shape is maintained.
2: A hemisphere is formed, but some trace of the as-extruded shape remains.
3: A hemisphere is formed, and its shape is maintained.
4: A hemisphere is formed, but its height is slightly low.
5: A hemisphere is not formed or, if a hemisphere is formed, it immediately crushes.

Test Example 6 (Handling Properties)

In carrying out the formability test described above, the tip of the needle was positioned 1 to 2 cm above the glass sheet, the tip of the needle was moved upward after discharge of the paste, and the behaviors of the paste on the glass sheet and the paste adhering to the tip of the needle were visually checked. The handling properties of the paste were evaluated according to the evaluation criteria listed below.

[Evaluation Criteria of Handling Properties]
1: The paste is quickly separated from the tip of the needle, and the paste on the glass sheet forms a hemispherical shape.
2: The paste is entrained about 1 cm by, and then separated from, the tip of the needle, and the paste on the glass sheet forms a somewhat angular shape.
3: The paste is entrained 2 to 3 cm by, and then separated from, the tip of the needle, and the paste on the glass sheet forms an angular shape.
4: The paste is entrained 4 cm or more by, and then separated from, the tip of the needle, and the paste on the glass sheet forms an angular shape.

Test Example 7 (Flexural Strength)

Each of the prepared dental curable compositions (pastes) was defoamed under vacuum, and loaded into a mold made of stainless steel (having dimensions of 2 mm×2 mm×25 mm). Glass slides were pressed against the upper and lower surfaces of the composition, and each of the two surfaces was irradiated with light using a dental visible light irradiation device (Pencure 2000 manufactured by Morita Corporation) at five points for 10 seconds per each point, and thus the composition was cured. Five cured products were fabricated for each of Examples and Comparative Examples. Each cured product was stored in 37° C. distilled water for 24 hours after being taken out of the mold. The flexural strength of each of the specimens was measured using a universal testing machine (manufactured by Shimadzu Corporation, Product code "AGI-100") under conditions where the span was 20 mm and the crosshead speed was 1 mm/minute. The average of the values measured for the specimens was calculated, and defined as the flexural strength. A flexural strength of 130 MPa or more is acceptable.

Test Example 8 (Degree of Diffusion)

Each of the prepared dental curable compositions was loaded into a mold made of Teflon (having a diameter of 20 mm and a thickness of 0.5 mm). Glass slides were pressed against the upper and lower surfaces of the composition, and each of the upper and lower surfaces was irradiated with light using α-Light II (halogen light irradiation device manufactured by Morita Corporation) for 1 minute to cure the composition. The cured product was taken out of the mold, and then subjected to measurement of luminance distribution of transmitted light using a three-dimensional variable angle photometer (GP-200 manufactured by MURAKAMI COLOR RESEARCH LABORATORY). The degree of diffusion was calculated according to the previously-indicated formula (2).

Test Example 9 (Surface Hardness: Vickers Hardness)

An appropriate amount of each of the prepared dental curable compositions was placed on a glass slide, and the glass slide and another were pressed against the upper and lower surfaces of the composition by means of a 1 mm gauge (manufactured by Mitutoyo Corporation). Only the upper side was irradiated with light using a dental visible light irradiation device (Pencure 2000 manufactured by Morita Corporation) for 10 seconds to cure the composition. Thus, a disk-shaped cured product having a diameter of 10 mm and a thickness of 1 mm was fabricated. Its clean, smooth surface was polished with #1500 abrasive paper under dry conditions, and finally subjected to mirror polishing using a diamond paste. Using a microhardness tester (HM-221 manufactured by Mitutoyo Corporation), the Vickers hardness of the thus fabricated specimen was measured by applying a load of 200 g for 10 seconds. A surface hardness of 25 or more is acceptable.

Test Example 10 (Viscosity of Polymerizable Monomer)

The viscosity of each polymerizable monomer mixture was measured using a TV-30 viscometer (manufactured by Toki Sangyo Co., Ltd.) with a 0.8°×R24 cone rotor for a sample amount of 0.6 mL at 40° C. The measurement was started after 1-minute preheating, and the value obtained 5 minutes after the start of the measurement was defined as the viscosity.

TABLE 1

| Component (parts by weight) | | Example 1 | Example 2 | Example 3 | Example 4 | Example 5 | Example 6 | Example 7 | Example 8 | Example 9 |
|---|---|---|---|---|---|---|---|---|---|---|
| Inorganic particle | b-1 | 93 | 94 | 98 | | | | | 94 | 94 |
| | b-2 | | | | 94 | | | | | |
| | b-3 | | | | | 94 | | | | |
| | b-4 | | | | | | 94 | 94 | | |
| | c-1 | 7 | 6 | 2 | 6 | 6 | 6 | 6 | | |
| | c-2 | | | | | | | | 6 | |
| | c-3 | | | | | | | | | 6 |
| Polymerizable monomer | D2.6E | 23 | 23 | 23 | 23 | 25 | 23 | 23 | 23 | 23 |
| | 3G | 10 | 10 | 10 | 10 | 17 | 10 | 5 | 10 | 10 |
| | DD | | | | | | | 5 | | |
| Physical properties | Viscosity of polymerizable monomer (mPa · s) | 62 | 62 | 62 | 62 | 24 | 62 | 56 | 62 | 62 |
| | Refractive index after polymerization of polymerizable monomer | 1.549 | 1.549 | 1.549 | 1.549 | 1.543 | 1.549 | 1.548 | 1.549 | 1.549 |
| | Polishability (Gloss value) | 70 | 75 | 73 | 76 | 73 | 72 | 73 | 75 | 76 |
| | Gloss retention | 69 | 73 | 71 | 72 | 72 | 70 | 71 | 71 | 70 |
| | Surface hardness | 25.2 | 31.5 | 30.2 | 33.2 | 32.6 | 28.8 | 29.8 | 31.2 | 33.8 |
| | Formability | 2 | 3 | 3 | 3 | 3 | 3 | 3 | 3 | 4 |
| | Handling properties | 1 | 1 | 2 | 1 | 2 | 2 | 1 | 1 | 1 |
| | Discharge performance (N) | 38 | 27 | 25 | 26 | 22 | 19 | 25 | 24 | 16 |
| | Consistency (mm) | 26 | 29 | 26 | 28 | 32 | 31 | 33 | 27 | 43 |
| | Degree of diffusion | 0.351 | 0.395 | 0.121 | 0.373 | 0.381 | 0.378 | 0.365 | 0.399 | 0.008 |
| | Flexural strength (MPa) | 140 | 141 | 135 | 141 | 142 | 140 | 144 | 142 | 135 |

TABLE 2

| Component (parts by weight) | | Example 10 | Example 11 | Example 12 | Example 13 | Example 14 | Example 15 | Example 16 |
|---|---|---|---|---|---|---|---|---|
| Inorganic particle | b-1 | 94 | 94 | 93 | 96 | 93 | 96 | 95 |
| | c-1 | | | 7 | 4 | 7 | 4 | 5 |
| | c-4 | 6 | | | | | | |
| | c-5 | | 6 | | | | | |

TABLE 2-continued

| Component (parts by weight) | | Example 10 | Example 11 | Example 12 | Example 13 | Example 14 | Example 15 | Example 16 |
|---|---|---|---|---|---|---|---|---|
| Polymerizable monomer | D2.6E | 23 | 23 | 19 | 23 | 34 | 27 | 35 |
| | 3G | 10 | 10 | 6 | 10 | 14 | 12 | 15 |
| | Bis-GMA | | | | | | 1 | |
| Physical properties | Viscosity of polymerizable monomer (mPa·s) | 62 | 62 | 80 | 62 | 63 | 56 | 62 |
| | Refractive index after polymerization of polymerizable monomer | 1.549 | 1.549 | 1.553 | 1.549 | 1.550 | 1.549 | 1.549 |
| | Polishability (Gloss value) | 75 | 76 | 74 | 70 | 70 | 71 | 69 |
| | Gloss retention | 71 | 71 | 69 | 68 | 69 | 69 | 70 |
| | Surface hardness | 30.9 | 33.7 | 32.3 | 26.2 | 25.7 | 27.7 | 25.0 |
| | Formability | 4 | 4 | 2 | 4 | 4 | 4 | 4 |
| | Handling properties | 1 | 1 | 3 | 2 | 2 | 2 | 3 |
| | Discharge performance (N) | 18 | 16 | 34 | 19 | 14 | 21 | 17 |
| | Consistency (mm) | 41 | 40 | 25 | 41 | 45 | 41 | 44 |
| | Degree of diffusion | 0.006 | 0.008 | 0.451 | 0.388 | 0.375 | 0.410 | 0.378 |
| | Flexural strength (MPa) | 131 | 135 | 143 | 140 | 139 | 141 | 137 |

TABLE 3

| Component (parts by weight) | | Example 17 | Example 18 | Example 19 | Example 20 | Example 21 | Example 22 | Example 23 |
|---|---|---|---|---|---|---|---|---|
| Inorganic particle | b-1 | 94 | 94 | 94 | 94 | 94 | 94 | 94 |
| | c-1 | 6 | 6 | 6 | 6 | 6 | 6 | 6 |
| Polymerizable monomer | D2.6E | 23 | 25 | 25 | 25 | 25 | 25 | 28 |
| | 3G | | | | 2 | | | |
| | NPG | 10 | | | | 5 | 5 | |
| | HD | | 12 | | | | | |
| | DD | | | 12 | | | | |
| | UDMA | | | | 8 | | 5 | |
| | U-4TH | | | | | 5 | | 5 |
| Physical properties | Viscosity of polymerizable monomer (mPa·s) | 62 | 74 | 73 | 397 | 380 | 280 | 306 |
| | Refractive index after polymerization of polymerizable monomer | 1.546 | 1.550 | 1.549 | 1.548 | 1.550 | 1.551 | 1.554 |
| | Polishability (Gloss value) | 72 | 71 | 74 | 71 | 70 | 72 | 69 |
| | Gloss retention | 70 | 70 | 69 | 69 | 69 | 70 | 68 |
| | Surface hardness | 31.2 | 33.1 | 32.4 | 29.2 | 28.9 | 27.7 | 26.3 |
| | Formability | 3 | 4 | 4 | 2 | 2 | 2 | 2 |
| | Handling properties | 2 | 2 | 2 | 3 | 3 | 2 | 2 |
| | Discharge performance (N) | 18 | 16 | 14 | 33 | 30 | 25 | 27 |
| | Consistency (mm) | 39 | 40 | 40 | 33 | 35 | 36 | 35 |
| | Degree of diffusion | 0.352 | 0.341 | 0.342 | 0.355 | 0.298 | 0.331 | 0.312 |
| | Flexural strength (MPa) | 131 | 132 | 141 | 135 | 132 | 139 | 135 |

TABLE 4

| Component (parts by weight) | | Comparative Example 1 | Comparative Example 2 | Comparative Example 3 | Comparative Example 4 | Comparative Example 5 | Comparative Example 6 |
|---|---|---|---|---|---|---|---|
| Inorganic particle | b-1 | 92 | | 100 | | 94 | 94 |
| | b-5 | | 94 | | | | |
| | b-6 | | | | 94 | | |
| | c-1 | 8 | 6 | | 6 | | |
| | c-6 | | | | | 6 | |
| | c-7 | | | | | | 6 |
| Polymerizable monomer | D2.6E | 23 | 23 | 23 | 23 | 23 | 23 |
| | 3G | 10 | 10 | 10 | 10 | 10 | 10 |
| Physical properties | Viscosity of polymerizable monomer (mPa·s) | 62 | 62 | 62 | 62 | 62 | 62 |
| | Refractive index after polymerization of polymerizable monomer | 1.549 | 1.549 | 1.549 | 1.549 | 1.549 | 1.549 |
| | Polishability (Gloss value) | 67 | 58 | 71 | 70 | 71 | 56 |
| | Gloss retention | 64 | 55 | 71 | 70 | 69 | 54 |
| | Surface hardness | 20.5 | 20.0 | 27.5 | 26.0 | 28.0 | 19.5 |
| | Formability | 2 | 2 | 5 | 1 | 5 | 3 |
| | Handling properties | 1 | 1 | 4 | 1 | 4 | 1 |
| | Discharge performance (N) | 43 | 33 | 18 | 60 | 19 | 24 |
| | Consistency (mm) | 24 | 23 | 34 | 13 | 35 | 33 |
| | Degree of diffusion | 0.491 | 0.381 | 0.007 | 0.481 | 0.371 | 0.371 |
| | Flexural strength (MPa) | 135 | 135 | 124 | 139 | 138 | 117 |

It can be seen that, as shown in the tables, the dental curable compositions of the present invention (Examples 1 to 23) had a high initial hardness and flexural strength, had excellent polishability, and also had high gloss retention (gloss value after toothbrush abrasion test). It can also be seen that the compositions of Examples 1 to 8 and 12 to 23 had high light diffusing property, and were excellent in terms of color conformity. It can be seen that the compositions of Examples 1 to 8 were excellent particularly in formability, and had excellent quality particularly as resins of the low-flow type. It can also be seen that the compositions of Examples 13 to 16 required only a particularly low discharge force, and had excellent quality particularly as resins of the high-flow type which need to have high flowability.

INDUSTRIAL APPLICABILITY

The dental curable composition of the present invention can be suitably used as a substitute for a part or the whole of a natural tooth in the field of dentistry, and is best suited as a flowable composite resin.

The invention claimed is:

1. A dental curable composition comprising:
a polymerizable monomer (A), which is a (meth)acrylic acid ester;
irregularly-shaped inorganic particles (B) having an average particle diameter of 0.1 to 0.3 μm and surface-treated with a silane coupling agent (a) represented by the following formula (1):

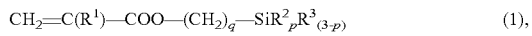  (1), wherein $R^1$ represents a hydrogen atom or a methyl group, $R^2$ represents a hydrolyzable group, $R^3$ represents a hydrocarbon group having 1 to 6 carbon atoms, p is an integer of 2 or 3, and q is an integer of 8 to 13; and
inorganic ultrafine particles (C) having an average particle diameter of 5 to 50 nm and surface-treated with a silane coupling agent (b) represented by a formula that is the same as the formula (1) representing the silane coupling agent (a) except that q is an integer of 1 to 6, wherein
the dental curable composition comprises 25 to 50 parts by weight of the polymerizable monomer (A), per 100 parts by weight of the amount of total inorganic particles,
the dental curable composition comprises 92.5 to 98 weight % of the irregularly-shaped inorganic particles (B) and 2 to 7.5 weight % of the inorganic ultrafine particles (C) relative to the amount of total inorganic particles, and
the dental curable composition has a consistency of 25 to 55.

2. The dental curable composition according to claim 1, wherein the polymerizable monomer (A) has a refractive index after polymerization of 1.52 to 1.58, the irregularly-shaped inorganic particles (B) have a refractive index of 1.52 to 1.58, and the inorganic ultrafine particles (C) have a refractive index of 1.43 to 1.50.

3. The dental curable composition according to claim 1, wherein the inorganic ultrafine particles (C) are present in the form of agglomerated particles, and the agglomerated particles have an average particle diameter of 1 to 10 μm.

4. A dental flowable composite resin comprising the dental curable composition according to claim 1.

5. A package comprising a container holding the dental flowable composite resin according to claim 4 and a needle tip to be attached to a tip of the container.

6. A dental flowable composite resin comprising the dental curable composition according to claim 2.

7. A dental flowable composite resin comprising the dental curable composition according to claim 3.

8. A package comprising a container holding the dental flowable composite resin according to claim 6 and a needle tip to be attached to a tip of the container.

9. A package comprising a container holding the dental flowable composite resin according to claim 7 and a needle tip to be attached to a tip of the container.

10. The dental curable composition according to claim 1, wherein the irregularly-shaped inorganic particles (B) are surface treated with at least one silane coupling agent selected from the group consisting of 11-methacryloyloxyundecyltrimethoxysilane, 8-methacryloyloxyoctyltrimethoxysilane, and 13-methacryloyloxytridecyltrimethoxysilane.

11. The dental curable composition according to claim 1, wherein the inorganic ultrafine particles (C) are surface treated with 3-methacryloxypropyltrimethoxysilane.

12. The dental curable composition according to claim 1, wherein the polymerizable monomer (A) is at least one selected from the group consisting of 2,2-bis(4-methacryloyloxypolyethoxyphenyl)propane, triethylene glycol dimethacrylate, 2,2-bis[4-(3-methacryloyloxy-2-hydroxypropoxy)phenyl]propane, 1,10-decanediol dimethacrylate, neopentyl glycol dimethacrylate, 1,6-hexanediol dimethacrylate, [2,2,4-trimethylhexamethylene bis(2-carbamoyloxyethyl)]dimethacrylate, and N,N'-(2,2,4-trimethylhexamethylene)bis[2-(aminocarboxy)propane-1,3-diol] tetramethacrylate.

13. The dental curable composition according to claim 1, wherein
the irregularly-shaped inorganic particles (B) are surface treated with at least one silane coupling agent selected from the group consisting of 11-methacryloyloxyundecyltrimethoxysilane, 8-methacryloyloxyoctyltrimethoxysilane, and 13-methacryloyloxytridecyltrimethoxysilane,
the inorganic ultrafine particles (C) are surface treated with 3-methacryloxypropyltrimethoxysilane, and
the polymerizable monomer (A) is at least one selected from the group consisting of 2,2-bis(4-methacryloyloxypolyethoxyphenyl)propane, triethylene glycol dimethacrylate, 2,2-bis[4-(3-methacryloyloxy-2-hydroxypropoxy)phenyl]propane, 1,10-decanediol dimethacrylate, neopentyl glycol dimethacrylate, 1,6-hexanediol dimethacrylate, [2,2,4-trimethylhexamethylene bis(2-carbamoyloxyethyl)] dimethacrylate, N,N'-(2,2,4-trimethylhexamethylene) bis[2-(aminocarboxy)propane-1,3-diol] tetramethacrylate.

14. The dental curable composition according to claim 1, wherein $R^2$ of formula (1) represents an alkoxy group.

15. The dental curable composition according to claim 1, wherein q is 3 for the silane coupling agent (b).

16. The dental curable composition according to claim 1, wherein
$R^2$ of formula (1) represents an alkoxy group, and
q is 3 for the silane coupling agent (b).

* * * * *